United States Patent [19]

Khan et al.

[11] 4,296,139

[45] Oct. 20, 1981

[54] BITTERING AGENTS

[75] Inventors: Riaz A. Khan, Sonning; Michael R. Jenner, Pangbourne, both of England

[73] Assignee: Talres Development (N.A.) N.V., Curacao, Netherlands Antilles

[21] Appl. No.: 85,402

[22] Filed: Oct. 17, 1979

[30] Foreign Application Priority Data

Oct. 18, 1978 [GB] United Kingdom ............... 41115/78

[51] Int. Cl.$^3$ ........................ A23L 1/226; A23L 2/00; A23L 2/02

[52] U.S. Cl. .................................. 426/536; 426/590; 426/599; 426/650; 426/658; 424/10; 252/366; 47/57.6; 536/122

[58] Field of Search ............... 426/590, 599, 534, 650, 426/560, 536; 536/122; 252/366; 424/10; 47/57.6

[56] References Cited

U.S. PATENT DOCUMENTS 1,280,150 10/1918 Brodsky ............................... 426/590
4,117,224 9/1978 Kahn et al. ......................... 536/122
4,133,903 1/1979 Thiele et al. ....................... 426/590

OTHER PUBLICATIONS

Evans et al., "Chem. Abst.", vol. 68, 1968, p. 87497(t).

*Primary Examiner*—Jeanette M. Hunter
*Attorney, Agent, or Firm*—Ostrolenk, Faber, Gerb & Soffen

[57] ABSTRACT

A new chlorinated sucrose derivative, 2,6,1',6'-tetrachloro-2,6,1',6'-tetradeoxy-mannosucrose, is used as a bittering agent, e.g. to replace quinine sulphate, in ingestible compositions such as Indian tonic water, and in non-ingestible compositions.

8 Claims, No Drawings

BITTERING AGENTS

This invention relates to a bittering agent for ingestible products.

By an ingestible product there is meant one which in the ordinary course of use is intended to be swallowed, for instance any foodstuff or beverage, or an orally administered pharmaceutical composition. The invention is particularly applicable to beverages.

In the United Kingdom, quinine sulphate is the only permitted bittering agent for use in such drinks as Indian tonic water and bitter lemon. Quinine is, however, of limited availability and also suffers from a susceptibility to degradation by ultra-violet light.

Many other bitter compounds are known, but they are not suitable for use in soft drinks for a variety of reasons, including lack of sufficient water solubility, an unpleasant flavour, etc.

A certain sucrose derivative has now been discovered to possess a strong bitter taste which makes it of considerable interest as a replacement for quinine. Some sucrose derivatives are already known to be bitter, the best known of which is sucrose octaacetate, which is used for denaturing alcohol. This compound does not, however, have the required degree of water solubility for use in soft drinks at low levels.

We have now discovered that a certain chlorosucrose derivative possesses a strong bittering action comparable with that of quinine sulphate, but appears to possess a significantly lower toxicity.

This is particularly surprising as other chlorosucrose derivatives are known to possess an intensely sweet taste. These sweet compounds possessing chlorine substituents at positions selected from the 4-,6-,1'- and 6'- positions are described in detail in, for example, West German OS No. 2700036 corresponding to British Patent Application No. 616/76. The new bitter compound, in contrast, possesses a chlorine substituent at the 2-position. The substitution by chlorine at the 2-position leads to inversion of the configuration at that position and thus the derivative is in fact a derivative of mannosucrose, that is to say α-D-mannopyranosyl-β-D-fructofuranoside.

According to the invention, there is provided a method of bittering composition by incorporating therein a bittering amount of 2,6,1',6'-tetrachloro-2,6,1',6'-tetradeoxy mannosucrose i.e. 1,6-dichloro-1,6-dideoxy-β-D-fructofuranosyl 2,6-dichloro2,6-dideoxy-α-D-mannopyranoside. This compound has been found to have a bittering strength approximately the same as that of quinine sulphate and has no problems of water solubility. The composition is, in one embodiment of the invention, an ingestible composition.

The invention also includes ingestible and other compositions containing 2,6,1',6'-tetrachloro-2,6,1',6'-tetradeoxy mannosucrose, and the invention further includes 2,6,1',6'-tetradeoxy mannosucrose per se.

The compound may be prepared by reacting 3,4,3',4'-tetra-O-acetyl-6,6'-dichloro-6,6'-dideoxysucrose with sulphuryl chloride in pyridine and chloro form at about $-7°$ C. to give the corresponding 2-chlorosulphate derivative, and treating this chlorosulphate derivative with lithium chloride in hexamethylphosphoramide, followed by removal of the blocking ester groups.

The tetrachloromannosucrose may be incorporated into any ingestible product at levels sufficient to give the desired bittering effect. As a straight replacement for quinine sulphate, for example, in Indian tonic water and bitter lemon drinks, it may be used at approximately the same level since its bitterness is approximately equal on a weight for weight basis. Any variation in comparative bitterness (for example, caused by effects of different flavouring agents) can be readily quantified and an adjustment made accordingly. Thus, for example, the chloromannosucrose can be incorporated in to a beverage such as Indian tonic water at a level from 0.005 to 0.01, e.g. of about 0.006 to 0.007%, by weight. Alternatively it may be incorporated into a concentrate for dilution, at an appropriately higher level. Other prospective substrates include confectionery (e.g. bitter chocolate) and aperitives.

Alternatively, the compound may be incorporated at higher levels into non-ingestible products to render them unpalatable, e.g. industrial alcohol, seeds which might be eaten by vermin or birds, etc.

The following examples illustrate the invention.

EXAMPLE 1

2,6,1',6'-tetrachloro-2,6,1',6'-tetradeoxy mannosucrose (a)

2,6,1',6'-tetrachloro-2,6-1',6'-tetradeoxymannosucrose tetra-acetate

A solution of 3,4,3',4'-tetra-O-acetyl-6,6'-dichloro-6,6'-dideoxy sucrose (Khan et al, Carbohydrate Res., 49 (1976) 259–264) (5 g) in pyridine (25 ml) and chloroform (75 ml) was treated with sulphuryl chloride (2.5 ml) at $-75°$. The reaction mixture was poured in ice-cold sulphuric acid (10%, 500 ml) with vigorous shaking and then extracted with dichloromethane. The organic layer was washed successively with water, aqueous sodium hydrogen carbonate water and dried ($Na_2SO_4$). The solution was concentrated to a syrup which was crystallised from ether-light petroleum to give the 1',2-bis (chlorosulphate) (5.4 g, 80%). The 1',2-bis chlorosulphate (4 g) was then treated with lithium chloride (4 g) in hexamethylphosphoric triamide (30 ml) at 80° for 20 h. The reaction mixture was worked up as described above to give a syrup. Elution of the syrup from a column of silica gel (100 g), using ether-light petroleum (1:1), gave the 2,6,1',6'-tetrachloride (2.7 g, 85%) as a syrup $[\alpha]_D -16.7°$ (c 1.01, chloroform) -N.m.r. data ($CDCl_3$): 4.40 (d,$J_1$, 2 2.) Hz, h-1); 5.57 (q,$J_{2,34}$.0H-2); 4.34–4.60 (m, 2 protons, H-3', h-4'); 6.10–6.51 (6 protons, H-6, h-1', H-6'); 7.78–7.88 (12 protons, 4 Ac). Mass spectral data: [Ions are 9:6:1 triplets due to two chlorine atoms] m/e 283, 233, 163.

Anal. Calc. for $C_{20}H_{26}Cl_4O_{11}$. C, 41.1; H, 4.49; Cl, 24.3. Found: C, 42.1; H, 4.75; Cl, 24.1.

(b) 2,6,1',6',-Tetrachloro-2,6,1',6'-tetradeoxy mannosucrose

A solution of the tetrachloride tetra-acetate (1 g) in dry methanol was treated with a catalytic amount of sodium methoxide at room temperature for 20 h. The solution was deionised with Amberlyst 15 (Trade Mark) resin and concentrated to afford 2,6,1',6'-tetrachloro-2,6,1',6'-tetradeoxy mannosucrose (0.64 g, 90%) as a syrup $[\alpha] +22.4°$ (c 0.93, methanol).

Anal. Calc. for $C_{12}H_{18}Cl_4O_7$; C, 34.6; H, 4.36 Found: C, 35.2: H,4.68.

EXAMPLE 2

Comparison of absolute taste thresholds of quinine sulphate and 2,6,1',6',-tetrachloro-2,6,1',6'-tetradeoxymannosucrose Threshold is defined as a statistically determined point on the stimulus scale at which occurs a transition in a series of sensations or judgements. Absolute threshold is defined as the magnitude of stimulus at which a transition occurs from "no sensation" to "sensation".

The experiment was carried out to compare the taste thresholds of the two bitter compounds using the Rating Scale method proposed by R. A. M. Gregson, J. Lyons & Company Limited 1962. The procedure is a combination of the ascending series method and a rating scale method.

Method

A solution was made up by dissolving 0.256 g quinine sulphate in 500 ml of water. Dilutions were made from this solution, each dilution being half the concentration of the previous one. Similarly 0.0104 g of the chlorosucrose derivative was dissolved in 40 ml of water and further dilutions were made from this solution.

| Quinine | Chlorosucrose derivative | | |
|---|---|---|---|
| | % (g/100g) | | % (g/100g) |
| J 0.256 quinine/500ml H$_2$O | 0.0512 | 0.0104g/40ml H$_2$O | 0.026 |
| I 250ml/0.0512/250ml H$_2$O | 0.0256 | 20ml 0.026/20ml H$_2$O | 0.013 |
| H 250ml/0.0256/250ml H$_2$O | 0.0128 | 20ml 0.013/20ml | 0.0065 |
| G 250ml/0.0128/250ml H$_2$O | 0.0064 | 20ml 0.0065/20ml | 0.00325 |
| F 250ml/0.0064/20ml H$_2$O | 0.0032 | 20ml 0.00325/20ml | 0.00162 |
| E 250ml/0.0032/250ml H$_2$O | 0.00016 | 20ml 0.00162/20ml | 0.00032 |
| D 250ml/0.0016/250ml H$_2$O | 0.0008 | 20ml 0.00082/20ml | 0.00041 |
| C 250ml/0.008/250ml H$_2$O | 0.0004 | 20ml 0.0004/20ml | 0.0002 |
| B 250ml/0.0004/250ml H$_2$O | 0.0002 | 20ml 0.0002/20ml | 0.0001 |
| A H$_2$O | 0 | H$_2$O | 0 |

The solutions were presented to the taste panelists in increasing order of concentration starting with plain tap water. The solutions were labelled from A to J. A small amount of each solution was placed in a plastic cup. A mouthwash of plain water was made available so that each panelist could rinse his/her mouth between samples. Four panelists tasted the quinine sulphate solution and the same four tasted the chlorosucrose derivative as well. (There was not enough compound available for more panelists to taste chlorosucrose derivative). The panelists were asked to taste each solution starting with water in alphabetical order, and to give each solution a score according to the following table. Once the panelist had scored 7 he/she was asked to stop testing.

| Description | Score |
|---|---|
| Same as water | 1 |
| Doubtful if pure water | 2 |
| A very faint taste can't say what | 3 |
| A very faint bitter taste | 4 |
| A faint bitter taste | 5 |
| A weak bitter taste | 6 |
| A clear bitter taste | 7 |

Results

| Quinine Sulphate | | | Chlorosucrose Derivative | | |
|---|---|---|---|---|---|
| Conc. of Soln. % | Panelist 1 2 3 4 | Threshold Cumulative Proportion | Conc. of Soln. % | Panelist 1 2 3 4 | Threshold Cumulative Proportion |
| A H$_2$O | 2 1 1 1 | 0 | H$_2$O | 2 1 1 1 | 0 |
| B 0.0002 | 2 1 2 1 | 0 | 0.0001 | 2 1 1 1 | 0 |
| C 0.0004 | 2 3 2 2 | 0 | 0.0002 | 3 1 1 1 | 0 |
| D 0.0008 | 3 <u>6</u> 2 3 | 0.25 | 0.00041 | <u>4</u> 1 2 2 | 0.25 |
| E 0.0016 | 3 <u>7</u> 3 <u>4</u> | 0.5 | 0.00082 | <u>4</u> 1 <u>4</u> 3 | 0.5 |
| F 0.0032 | <u>4</u> 5 <u>6</u> | 1.0 | 0.00162 | <u>4</u> 1 <u>4</u> 3 | 0.5 |
| G 0.0064 | 5–7 7 | 1.0 | 0.00325 | <u>4</u> <u>4</u> <u>4</u> 3 | 0.75 |
| H 0.0128 | 7 | | 0.0065 | 5 6 <u>4</u> <u>4</u> | 1.0 |
| I 0.0256 | | | 0.013 | 6 7 7 5 | 1.0 |
| J 0.0512 | | | 0.026 | 7 7 | |

N.B. The taste score is underlined on the first occasion it reaches 4 or more (the threshold). The panelists 1, 2, 3 and 4 are the same in each test.

The threshold cumulative proportion is the proportion of the panel able to taste a very faint bitter taste (score 4) e.g. when the proportion is 0.25, 1 panelist out of four can taste a bitter taste (score 4 or more) and when the cumulative score is 1, all panelists can taste a bitter taste.

Threshold cumulative proportion = $\frac{\text{no. panelists scoring 4 or more}}{\text{number of panelists participating}}$ Graphs were drawn for quinine sulphate and the chlorosucrose derivative showing cumulative proportions of thresholds against concentration strength. Each threshold proportion was located midway between the adjacent stimuli. The absolute thresholds were read from the graphs at the fiftieth percentile (i.e. the concentration at which 50% of the tasters can detect bitterness).

From the graphs the thresholds were:

| For quinine sulphate | 0.00193% | = 19.3 ppm |
|---|---|---|
| For chlorosucrose derivative | 0.002% | = 20 ppm |

Discussion

From the results it appears that the chlorosucrose derivative has a bitterness of a similar magnitude to quinine sulphate on a weight to weight basis.

On a molar basis:

Quinine Sulphate has a molecular weight of 782.96.

A 0.00166% solution contains 0.00166 g/100 g $H_2O = 0.016$ g/liter which is equivalent to $$\frac{0.0166}{782.96} = 0.0000212 = 2.12 \times 10^{-5} M.$$

The chlorosucrose derivative has a molecular weight of 414. A 0.002% solution contains 0.002 g/100 g = 0.02 g liter which is equivalent to $$\frac{0.02}{414} = 0.0000483 = 4.83 \times 10^{-5} M.$$

According to these results, it appears that the two compounds at very low levels of concentration give a bitter taste with a similar threshold value. A higher molar concentration of chlorosucrose derivative is required to give a similar result to quinine sulphate. The results obtained are, of course, based on a very small taste panel size so absolute accuracy cannot be expected, but a relative ranking is possible.

Taste threshold values for quinine sulphate were stated by Pfaffmann (Handbook of Physiology vol. 1) to be in the range $$4 \times 10^{-7} M \text{ (0.3 ppm) to } 1.1 \times 10^{-5} M \text{ (8.6 ppm)}$$

with a median of $$8 \times 10^{-6} M \text{ (6.3 ppm)}$$

Variances in threshold value can be due to differences in the technique employed, impurities in the chemicals, inadequate number of tests, order of presentation, temperature, noise, time of day, experience and range of concentrations. More significant results would be obtained with a larger panel, preferably trained, with more concentrations around the expected threshold value.

Conclusion 2,6,1,6-Tetra-chloro-2,6,1,6-tetradeoxymannosucrose has a bitter taste which can be recognised at a molar concentration in the region of $4.83 \times 10^{-5} M$ and is thus of interest as an alternative to quinine sulphate in food products e.g. soft drinks.

EXAMPLE 3

Indian Tonic Water

A conventional formulation has the following ingredients:

|  | % by weight of finished drink |
|---|---|
| benzoic acid | 0.08 |
| citric acid | 0.167 |
| sugar | 7.0 |
| saccharin | 0.008 |
| flavour | 0.1 |
| quinine sulphate | 0.0057012 |

An equally bitter amount of 2,6,1',6',-tetrachloro-2,6,1',6'-tetradeoxy mannosucrose, say 0.006 or 0.007% by weight, can be substituted for the quinine sulphate to give a comparable drink. The tetrachloromannosucrose can also be incorporated in a non-caloric tonic water containing a higher proportion of saccharin and no sugar.

We claim:

1. In a method of bittering a substance by incorporating therein an effective amount of a bittering agent, the improvement which comprises employing 2,6,1',6'-tetrachloro-2,6,1',6'-tetradeoxymannosucrose as said bittering agent.

2. A method according to claim 1, in which the substance is an ingestible.

3. A method according to claim 2 in which 2,6,1',6'-tetrachloro-2,6,1',6'-tetradeoxy-mannosucrose is incorporated into a beverage at a level of from 0.005 to 0.01% by weight.

4. An ingestible composition containing an effective amount of 2,6,1',6'-tetrachloro-2,6,1',6'-tetradeoxy-mannosucrose as a bittering agent.

5. A composition according to claim 4, in the form of a beverage.

6. A composition according to claim 4, which is Indian tonic water or bitter lemon.

7. A concentrate for dilution to form an ingestible product, comprising an effective amount of 2,6,1',6'-tetrachloro-2,6,1',6'-tetradeoxy-mannosucrose as a bittering agent, together with at least one flavouring, sweetening or stabilising agent.

8. A non-ingested composition comprising 2,6,1',6'-tetrachloro-2,6,1',6'-tetradeoxymannosucrose as a bittering agent in an amount sufficient to render said non-ingestible composition unpalatable.

* * * * *